(12) United States Patent
Feitisch et al.

(10) Patent No.: US 9,166,364 B2
(45) Date of Patent: Oct. 20, 2015

(54) SEMICONDUCTOR LASER MOUNTING WITH INTACT DIFFUSION BARRIER LAYER

(75) Inventors: Alfred Feitisch, Los Gatos, CA (US); Gabi Neubauer, Los Gatos, CA (US); Mathias Schrempel, Alta Loma, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 383 days.

(21) Appl. No.: 13/212,085

(22) Filed: Aug. 17, 2011

(65) Prior Publication Data
US 2013/0044322 A1    Feb. 21, 2013

(51) Int. Cl.
*H01S 3/04* (2006.01)
*H01S 5/022* (2006.01)
(Continued)

(52) U.S. Cl.
CPC ............ *H01S 5/02272* (2013.01); *H01L 24/03* (2013.01); *H01L 24/05* (2013.01); *H01L 24/29* (2013.01); *H01L 24/32* (2013.01); *H01L 24/83* (2013.01); *H01L 2224/0383* (2013.01); *H01L 2224/04026* (2013.01); *H01L 2224/0567* (2013.01); *H01L 2224/0568* (2013.01); *H01L 2224/05573* (2013.01); *H01L 2224/05624* (2013.01); *H01L 2224/05663* (2013.01); *H01L 2224/05664* (2013.01); *H01L 2224/05666* (2013.01); *H01L 2224/05669* (2013.01); *H01L 2224/05681* (2013.01); *H01L 2224/05684* (2013.01); *H01L 2224/05686* (2013.01);
(Continued)

(58) Field of Classification Search
CPC  H01S 5/02212; H01S 5/02272; H01S 5/0425
USPC .......................................... 372/34, 36; 257/99
See application file for complete search history.

(56) References Cited

U.S. PATENT DOCUMENTS 5,561,322 A * 10/1996 Wilson .......................... 257/703
5,794,839 A    8/1998 Kimura et al.
(Continued)

FOREIGN PATENT DOCUMENTS

DE       102006057718 A1    6/2008
WO       WO-9954923 A1     10/1999
WO       WO-2012125752 A1   9/2012

OTHER PUBLICATIONS

Tandon, et al., "Metallization Systems for Stable OHMIC Contacts to GaAs", Proceedings of the Workshop on Tungsten and Other Refractory Metals for VLSI Applications, Oct. 7, 1985.
(Continued)

*Primary Examiner* — Yuanda Zhang
(74) *Attorney, Agent, or Firm* — Mintz Levin Cohn Ferris Glovsky and Popeo, P.C.

(57) ABSTRACT

A first contact surface of a semiconductor laser chip can be formed to a target surface roughness selected to have a maximum peak to valley height that is substantially smaller than a barrier layer thickness. A barrier layer that includes a non-metallic, electrically-conducting compound and that has the barrier layer thickness can be applied to the first contact surface, and the semiconductor laser chip can be soldered to a carrier mounting along the first contact surface using a solder composition by heating the soldering composition to less than a threshold temperature at which dissolution of the barrier layer into the soldering composition occurs. Related systems, methods, articles of manufacture, and the like are also described.

18 Claims, 14 Drawing Sheets

(51) Int. Cl.
    *H01L 23/00*    (2006.01)
    *H01S 5/042*    (2006.01)

(52) U.S. Cl.
    CPC .............. *H01L2224/29109* (2013.01); *H01L 2224/29111* (2013.01); *H01L 2224/29139* (2013.01); *H01L 2224/29144* (2013.01); *H01L 2224/32245* (2013.01); *H01L 2224/83801* (2013.01); *H01S 5/02212* (2013.01); *H01S 5/0425* (2013.01)

(56) References Cited

U.S. PATENT DOCUMENTS

| | | | |
|---|---|---|---|
| 6,531,715 B1* | 3/2003 | Gerner | 257/81 |
| 2005/0167679 A1* | 8/2005 | Ishii et al. | 257/79 |
| 2007/0051968 A1* | 3/2007 | Yamamoto et al. | 257/99 |
| 2007/0064758 A1 | 3/2007 | Kuramoto et al. | |
| 2009/0092162 A1* | 4/2009 | Huff et al. | 372/36 |
| 2009/0196316 A1* | 8/2009 | Konig et al. | 372/36 |
| 2009/0294797 A1 | 12/2009 | Anzue et al. | |
| 2011/0032516 A1* | 2/2011 | Zhou et al. | 356/73 |

OTHER PUBLICATIONS

International Search Report and Written Opinion dated Jan. 8, 2013 for PCT app. No. PCT/US2012/050817.

Derek Hull, *Fractography: Observing, Measuring and Interpreting Fracture Surface Topography*, p. 128.

* cited by examiner even number 9,166,364 B2

SEMICONDUCTOR LASER MOUNTING WITH INTACT DIFFUSION BARRIER LAYER

CROSS-REFERENCE TO RELATED APPLICATIONS

This application is related to co-pending and co-owned U.S. patent application Ser. No. 13/026,921, filed on Feb. 14, 2011 and entitled "Spectrometer with Validation Cell" and also to co-pending and co-owned U.S. patent application Ser. No. 13/027,000, filed on Feb. 14, 2011, and entitled "Validation and Correction of Spectrometer Performance Using a Validation Cell." The disclosure of each application identified in this paragraph is incorporated by reference herein in its entirety.

TECHNICAL FIELD

The subject matter described herein relates to frequency stabilization of semiconductor lasers, in particular to mounting techniques for such lasers.

BACKGROUND

A tunable laser-based trace gas analyzer, such as for example a tunable diode laser absorption spectrometer (TDLAS) can employ a narrow line width (e.g. approximately single frequency) laser light source that is tuned across a trace gas absorption frequency range of a target analyte for each measurement of a sample volume of gas. Ideally, the laser light source in such an analyzer exhibits no material change in the starting and ending frequency of successive laser scans under a constant laser injection current and operating temperature. Additionally, long term stability of the frequency tuning rate of the laser as a function of the laser injection current, over the scan range, and over repetitive scans over a prolonged period of service can also be desirable.

Depending on the operational wavelength, however, currently available tunable laser sources (e.g. diode lasers and semiconductor lasers) can typically exhibit a wavelength drift on the order of a few picometers (on the order of gigahertz) per day to fractions of picometers per day. A typical trace gas absorption band line width can in some instances be on the order of a fraction of a nanometer to microns. Thus, drift or other variations in the output intensity of the laser light source can, over time, introduce critical errors in identification and quantification of trace gas analytes, particularly in gas having one or more background compounds whose absorption spectra might interfere with absorption features of a target analyte.

SUMMARY

In one aspect, a method includes forming a first contact surface of a semiconductor laser chip to a target surface roughness selected to have a maximum peak to valley height that is substantially smaller than a barrier layer thickness of a barrier layer (e.g. a diffusion barrier layer) to be applied to the first contact surface. The barrier layer, which includes a non-metallic, electrically conducting compound, is then applied to the first contact surface at that barrier layer thickness. The semiconductor laser chip is soldered to a carrier mounting using a solder composition. The soldering includes melting the soldering composition by heating the soldering composition to less than a threshold temperature at which dissolution of the barrier layer into the soldering composition occurs.

In an interrelated aspect, an article of manufacture includes a first contact surface of a semiconductor laser chip formed to a target surface roughness. The target surface roughness includes a maximum peak to valley height that is substantially smaller than a barrier layer thickness. The article of manufacture also includes a barrier layer having the barrier layer thickness applied to the first contact surface and a carrier mounting to which the semiconductor laser chip is soldered using a solder composition. The barrier layer includes a non-metallic, electrically conducting compound. The semiconductor laser chip is soldered to the carrier mounting along the first contact surface by a soldering process that includes melting the soldering composition by heating the soldering composition to less than a threshold temperature at which dissolution of the barrier layer into the soldering composition occurs.

In some variations one or more of the following features can optionally be included in any feasible combination. The barrier layer can remain contiguous subsequent to the soldering process such that no direct contact occurs between the solder composition and the materials of the semiconductor laser chip and/or such that no direct path exists by which constituents of any of the semiconductor laser chip, the solder composition, and the carrier mounting can diffuse across the barrier layer. Also subsequent to the soldering process, the solder composition can be characterized by substantially temporally stable electrical and thermal conductivities. In some examples, the solder composition used in the soldering process can be provided as a solder preform that is substantially non-oxidized. In other examples depositing the solder composition onto the heat sink or other carrier mounting, for example by evaporation, sputtering, or the like, can form a substantially non-oxidized solder composition. Additionally or alternatively, the soldering process can further include performing the melting of the soldering composition under a non-oxidizing or alternatively under a reducing atmosphere.

The threshold temperature can in some implementations be less than approximately 400° C., or optionally less than 370° C., or optionally less than 340° C., for example for solder compositions including but not limited to one or more of gold germanium (AuGe), gold silicon (AuSi), gold tin (AuSn), silver tin (AgSn), silver tin copper (AgSnCu), silver tin lead (AgSnPb), silver tin lead indium (AgSnPbIn), silver tin antimony (AgSnSb), tin lead (SnPb), lead (Pb), silver (Ag), silicon (Si), germanium (Ge), tin (Sn), antimony (Sb), bismuth (Bi), indium (In), and copper (Cu). Some non-limiting examples of solder compositions that may be compatible with implementations of the current subject matter are also listed below.

The forming of the first contact surface can include polishing the first contact surface to achieve the target surface roughness prior to applying the barrier layer. The target surface roughness can be less than approximately 100 Å rms or, alternatively, less than approximately 40 Å rms. A first thermal expansion characteristic of the carrier mounting can be matched to a second thermal expansion characteristic of the semiconductor laser chip. A metallization layer can be applied to the first contact surface prior to applying the at least one barrier layer, and a solder preparation layer can be applied to the first contact surface subsequent to applying the barrier layer and prior to the soldering process. The metallization layer can optionally include approximately 600 Å thickness of titanium, the barrier layer can optionally include approximately 1200 Å thickness of one or more of titanium nitride ($TiN_x$), titanium oxy-nitride ($TiN_xO_y$), cerium gadolinium oxy-nitride ($CeGdO_yN_x$), cerium oxide ($CeO_2$) tungsten nitride ($WN_x$), and/or another non-metallic, electrically-conducting compound; and the solder preparation layer can optionally include approximately 2000 to 5000 Å thickness of gold. In another implementation, the barrier layer can optionally include a second metallic barrier layer including but not limited to platinum (Pt), palladium (Pd), nickel (Ni), tungsten (W), molybdenum (Mo) and metals: and the solder preparation layer can optionally contain approximately 2000 to 5000 Å of gold (Au). Furthermore, the metallic barrier layer can be applied directly to the first metallization layer and the non-metallic barrier layer can be applied to the metallic barrier layer. In an alternative implementation the non-metallic barrier layer can be applied to the first metallization layer and the metallic barrier layer can be applied to the non-metallic barrier layer.

A solder facilitation layer can optionally be added between the first contact surface and a second contact surface on the carrier mounting prior to the soldering process. The solder facilitation layer can optionally include a metal that is not a component of a solder preparation layer on either of the first contact surface or on a second contact surface of the carrier mounting. In this context, the term "solder preparation layer" is understood to refer to a topmost layer on either or both of the first contact surface and the second contact surface prior to the addition of the solder facilitation layer. In various optional variations, the solder preparation layer can be a barrier layer, a metallization layer, or some other layer. The adding of the solder facilitation layer can optionally include at least one of placing a sheet of the metal that is not a component of the solder preparation layer between the first contact surface and the second contact surface prior to the soldering, and depositing a layer of the metal that is not a component of the solder preparation layer onto one or both of the first contact surface and the second contact surface prior to the soldering.

An apparatus, which can in some implementations be a tunable diode laser absorption spectrometer, can further include a light source that includes the carrier mounting and the semiconductor laser chip, a detector that quantifies a received intensity of light emitted from the light source along a path length, at least one of a sample cell and a free space volume through which the path length passes at least once, and at least one processor that performs operations comprising controlling a driving current to the laser source and receiving intensity data from the detector. The carrier mounting can include and/or act as a heat spreader, heat sink, or the like. The at least one processor can optionally cause the laser source to provide light having a wavelength modulation frequency and can demodulate the intensity data received from the detector to perform a harmonic spectroscopy analysis method. The at least one processor can mathematically correct a measurement spectrum to account for absorption by compounds in a sample gas through which the path length passes. In some examples, the mathematical correction can include subtraction of a reference spectrum from the measurement spectrum where the reference spectrum is collected for a sample of the sample gas in which a concentration of a target analyte has been reduced.

Systems and methods consistent with this approach are described as well as articles that comprise a tangibly embodied machine-readable medium operable to cause one or more machines (e.g., computers, etc.) to result in operations described herein. Similarly, computer systems are also described that may include a processor and a memory coupled to the processor. The memory may include one or more programs that cause the processor to perform one or more of the operations described herein.

The current subject matter may, in some implementations, provide one or more advantages. For example, because soldering temperatures can be elevated without causing excessive damage to a diffusion barrier layer, the use of lower temperature, lead-based solders can be avoided. This feature can enhance compliance with the Restriction of Hazardous Substances Directive (promulgated in the European Union) and other similar regulations, advisories, or the like regarding minimization of the use of lead. Solder compositions containing gold also generally provide better solder joint contiguity and surface wetting when gold plated surfaces are being joined. Because gold-containing solders typically require higher soldering temperatures, the use of a high temperature barrier layer that can survive such conditions without being substantially degraded can be quite beneficial.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain one or more features or the principles associated with the disclosed implementations. In the drawings.

DETAILED DESCRIPTION

Experimental data have revealed that laser emission wavelength changes as small as 1 picometer (pm) or less between spectral scans in a laser absorption spectrometer using a scannable or tunable laser source can materially alter a trace gas concentration determination with respect to a measurements obtainable with a spectral analyzer in its original calibration state. An example of spectral laser spectroscopy using a differential spectroscopy approach is described in co-owned U.S. Pat. No. 7,704,301, the disclosure of which is incorporated herein in its entirety. Other experimental data have indicated that a tunable diode laser-based analyzer designed for low analyte concentration detection and quantification (e.g. on the order of parts per million (ppm) of hydrogen sulfide ($H_2S$) in natural gas) and employing a harmonic (e.g. 2 f) wavelength modulation spectral subtraction approach can unacceptably deviate from its calibration state due to a shift in laser output of as small as 20 picometers (pm) at constant injection current and constant temperature (e.g. as controlled by a thermoelectric cooler).

In general terms, a laser frequency shift that can be acceptable for maintaining an analyzer calibration within its accuracy specification drops with smaller target analyte concentrations and also with increasing spectral interferences from other components of a sample mixture at the location of the target analyte absorption. For measurements of higher levels of a target analyte in a substantially non-absorbing background, larger laser frequency shifts can be tolerated while maintaining the analyzer calibration state.

Figure 1:
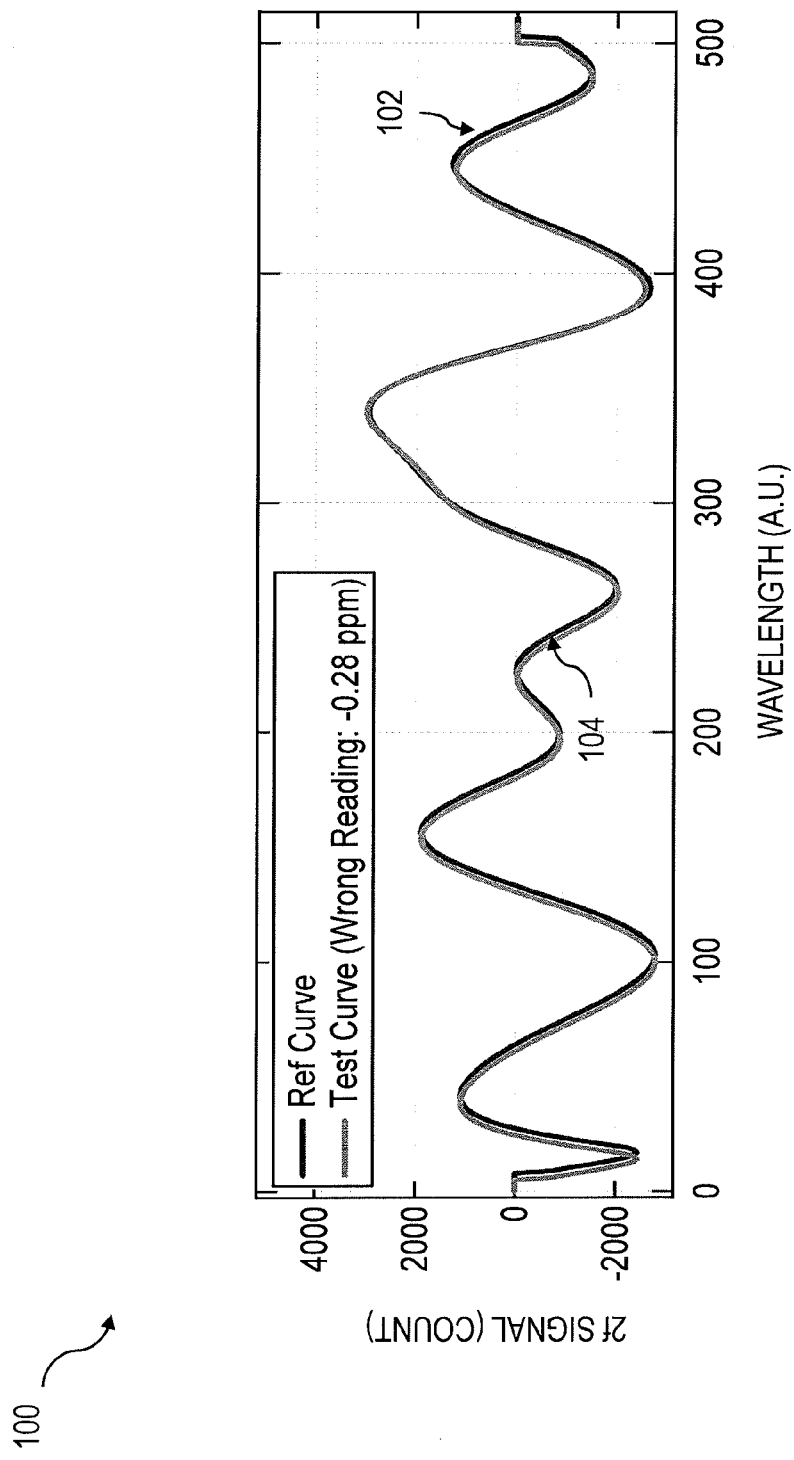
FIG. 1 is a graph illustrating effects of laser drift on performance of a laser absorption spectrometer.
Figure 2:
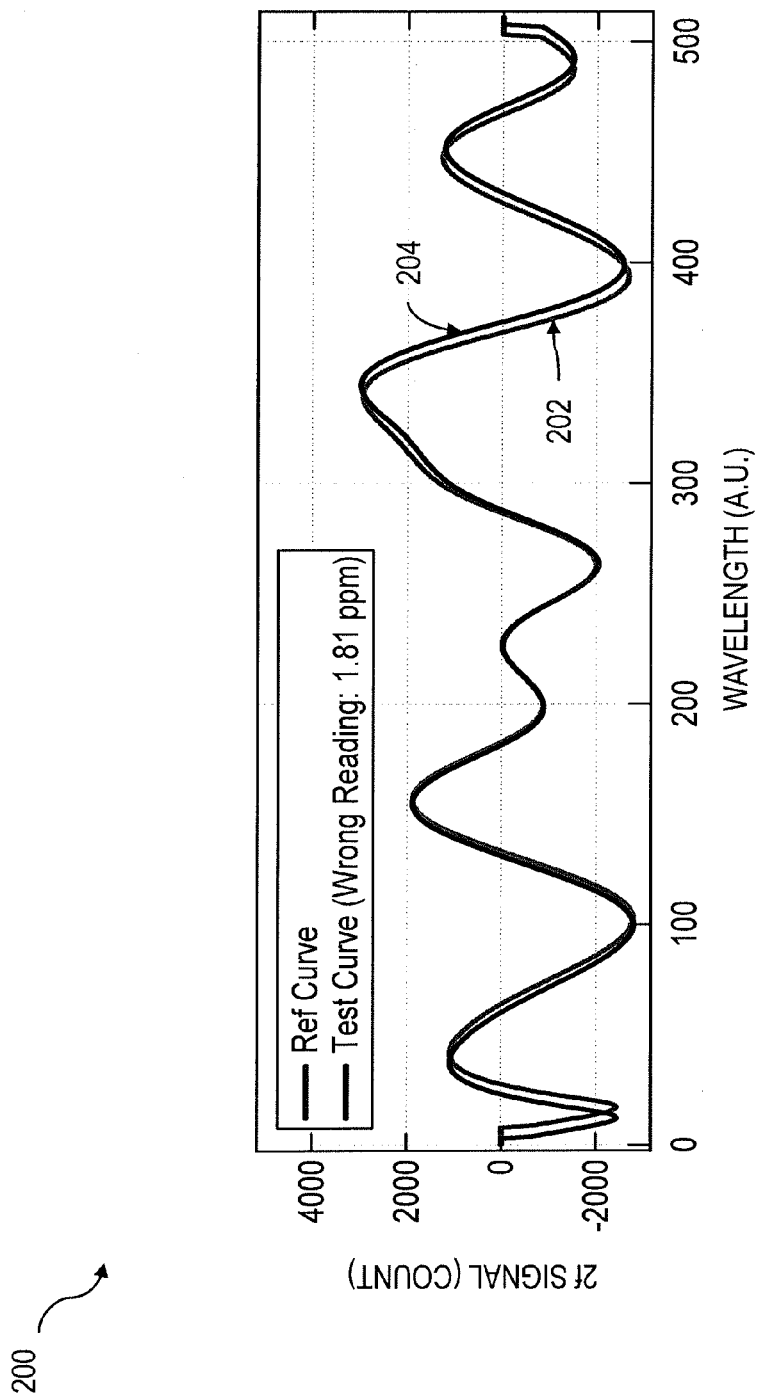
FIG. 2 is a second graph illustrating additional effects of laser drift on performance of a laser absorption spectrometer.

The graphs 100 and 200 shown in FIG. 1 and FIG. 2, respectively, show experimental data illustrating potential negative impacts of laser output variations that may be caused by changes in characteristics (e.g. physical, chemical, and the like) of a semiconductor laser source over time. The reference curve 102 shown in the graph 100 of FIG. 1 was obtained with a tunable diode laser spectrometer for a reference gas mixture containing approximately 25% ethane and 75% ethylene. The test curve 104 was obtained using the same spectrometer after some time had passed for a test gas mixture containing 1 ppm acetylene in a background of approximately 25% ethane and 75% ethylene. Acetylene has a spectral absorption feature in the range of about 300 to 400 on the wavelength axis of the chart 100 in FIG. 1. If the spectrometer were not adjusted in some manner to compensate for the drift observed in the test curve 104 relative to the reference curve 102, the measured concentration of acetylene from the spectrometer would be, for example, −0.29 ppm instead of the correct value of 1 ppm.

Similarly, in FIG. 2, the chart 200 shows a reference curve 202 obtained with a tunable diode laser spectrometer for a reference gas mixture containing approximately 25% ethane and 75% ethylene. The test curve 204 was obtained for a test gas mixture containing 1 ppm acetylene in a background of approximately 25% ethane and 75% ethylene. As shown in FIG. 2, the line shape of the test curve 204 is distorted relative to the line shape of the reference curve 202 due to drift or other factors affecting performance of the laser absorption spectrometer over time. If the test curve 204 were not corrected to compensate for the distortion observed in the test curve 204 relative to the reference curve 202, the measured concentration of acetylene in the test gas mixture determined by the spectrometer would be, for example, 1.81 ppm instead of the true concentration of 1 ppm.

Based on Ohm's Law (i.e. $P=I^2R$ where P is the power, I is the current, and R is the resistance), a current-driven semiconductor laser chip will generate waste heat that increases approximately as the square of the injection current driving the laser. While the resistance, R, of the semiconductor diode laser assembly is not typically linear or constant with changes in temperature, an approximately quadratic increase in waste heat with increases in current is generally representative of real-world performance. Thermal roll-over, in which the power output of a laser is reduced at excessive temperatures, can typically occur because the lasing efficiency of a typical band-gap type direct semiconductor laser diode decreases with increasing p-n junction operating temperature. This is especially true for infrared lasers, such as for example lasers based on indium phosphide (InP) or gallium antimonide (GaSb) material systems.

Single frequency operation of an infrared semiconductor laser can be achieved by employing DFB (distributed feedback) schemes, which typically use optical gratings, either incorporated in the laser ridge of the semiconductor laser crystal in the form of semiconductor crystal index of refraction periodicities or placed laterally to the laser ridge as metal bars. The effective optical periods of the approaches of the various gratings determining the laser emission wavelength can typically depend upon the physical spacing of the metal bars of the grating or upon the physical dimension of the ridge-regrown semiconductor material zones with different index of refraction and the index of refraction of the respective semiconductor materials. In other words, the emission wavelength of a semiconductor laser diode, such as are typically used for tunable diode laser spectroscopy, can depend primarily upon the laser p-n junction and on the laser crystal operating temperature and secondarily on the carrier density inside the laser. The laser crystal temperature can change the grating period as a function of the temperature dependent thermal expansion of the laser crystal along its long optical cavity axis and as a function of the temperature dependent index of refraction.

Typical injection current-related and temperature-related wavelength tuning rates of infrared lasers useable for tunable diode laser trace gas analyzers can be on the order of approximately 0.1 nanometers per ° C. and approximately 0.1 nanometers per milli-ampere. As such, it can be desirable to maintain semiconductor laser diodes for precision TDLAS devices at a constant operating temperature within a few thousandths of a ° C. and at injection currents that are controlled to within a few nano-amperes.

Long term maintenance and regeneration of a TDLAS calibration state and the related long term measurement fidelity with respect to the original instrument calibration can require the ability to substantially replicate the correct laser operating parameters in the wavelength space for any given measurement. This can be desirable for spectroscopy techniques employing subtraction of spectral traces (e.g. differential spectroscopy), such as is described in co-owned U.S. Pat. No. 7,704,301; pending U.S. patent application Ser. Nos. 13/027,000 and 13/026,091 and 12/814,315; and U.S. Provisional Application No. 61/405,589, the disclosures of which are incorporated by reference herein.

Commercially available single frequency semiconductor lasers that are suitable for trace gas spectroscopy in the 700 nm to 3000 nm spectral range have been found to generally exhibit a drift of their center frequency over time. Drift rates of several picometers (pm) to fractions of a pm per day have been confirmed by performing actual molecular trace gas spectroscopy over periods of 10 days to more than 100 days. Lasers that may behave as described can include, but are not limited to, lasers limited to single frequency operation by gratings etched into the laser ridge (e.g. conventional telecommunications grade lasers), Bragg gratings (e.g. vertical cavity surface emitting lasers or VCSELs), multiple layer narrow band dielectric mirrors, laterally coupled gratings, and the like. Frequency drift behavior has been observed with semiconductor diode lasers; VCSELs; horizontal cavity surface emitting lasers HCSEL's (HCSELs); quantum cascade lasers built on semiconductor materials including but not limited to indium phosphide (InP), gallium arsenide (GaAs), gallium antimonide (GaSb), gallium nitride (GaN), indium gallium arsenic phosphide (InGaAsP), indium gallium phosphide (InGaP), indium gallium nitride (InGaN), indium gallium arsenide (InGaAs), indium gallium aluminum phosphide (InGaAlP), indium aluminum gallium arsenide (InAlGaAs), indium gallium arsenide (InGaAs), and other single and multiple quantum well structures.

Approaches have been previously described to re-validate the performance of a tunable laser. For example, as described in U.S. patent application Ser. Nos. 13/026,921 and 13/027,000 referenced above, a reference absorption line shape collected during a calibrated state of an analyzer can be compared to a test absorption line shape collected subsequently. One or more operating parameters of the analyzer can be adjusted to cause the test absorption line shape to more closely resemble the reference absorption line shape.

Reduction of the underlying causes of frequency instability in semiconductor-based tunable lasers can also be desirable, at least because compensation of laser shift and outputted line shapes to maintain analyzer calibration by adjusting the semiconductor diode laser operating temperature or the median drive current may only be possible over limited wavelength shifts due to a typically non-linear correlation between injection current and frequency shift in semiconductor laser diodes (e.g. because of thermal roll-over as discussed above). The nonlinearity of the frequency shift as a function of injection current may change as a function of laser operating temperature set by a temperature control device (e.g. a thermoelectric cooler or TEC) and the median injection current. At higher control temperatures, thermal roll-over may occur at lower injection currents while at lower control temperatures, the roll-over may occur at higher injection currents. Because the control temperature and injection current combined determine the laser emission wavelength, not all combinations of control temperature and median injection current used to adjust the laser wavelength to the required target analyte absorption line will provide the same frequency scan and absorption spectra.

Accordingly, one or more implementations of the current subject matter relate to methods, systems, articles or manufacture, and the like that can, among other possible advantages, provide semiconductor-based lasers that have substantially improved wavelength stability characteristics due to a more temporally stable chemical composition of materials used in affixing a semiconductor laser chip to a mounting device. Some implementations of the current subject matter can provide or include a substantially contiguous and intact diffusion barrier layer that includes at least one non-metallic layer and alternatively at least one non-metallic and at least one metallic barrier layer at or near a contact surface between a semiconductor laser chip and a mounting surface. Drift of single frequency lasers can be reduced or even minimized, according to one or more implementations, by employing semiconductor laser designs, laser processing, electrical connections, and heat sinking features that reduce changes in heat conductivity, in stress and strain on the active laser, and in electrical resistivity of the injection current path over time.

Figure 3:
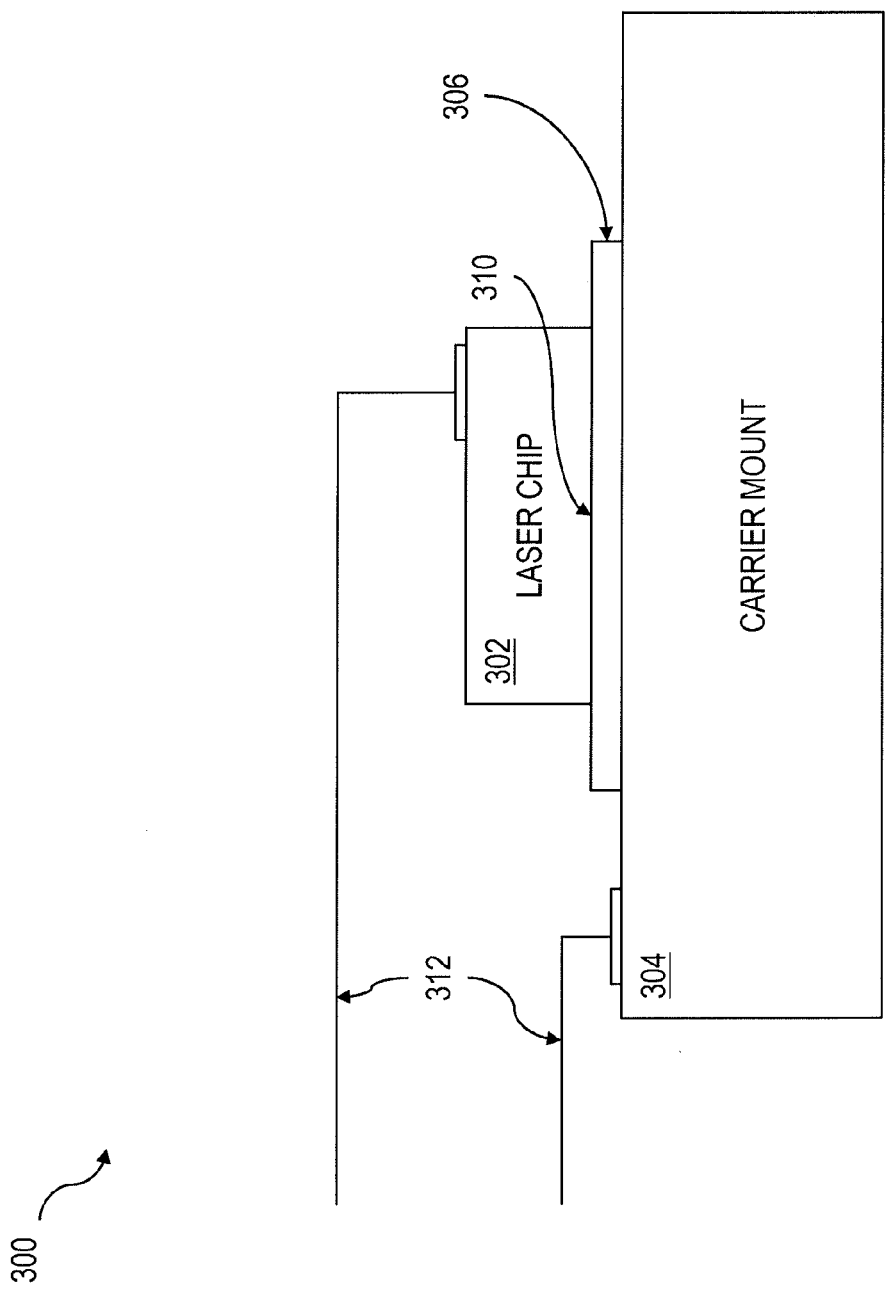
FIG. 3 is a schematic diagram illustrating a semiconductor laser chip secured to a carrier mount.

FIG. 3 illustrates an example of an apparatus 300 including a semiconductor laser chip 302 affixed to a mounting device 304 by a layer of solder 306 interposed between a contact surface 310 of the semiconductor laser chip 302 and the mounting device 304. The mounting device 304 can function as a heat sink and can provide one or more electrical connections to the semiconductor laser chip 302. One or more other electrical connections 312 can be provided to connect a p or n junction of the semiconductor laser chip 302 to a first polarity and the other junction to a second polarity, for example via conduction through the solder layer 306 into the carrier mount 304.

Figure 4:
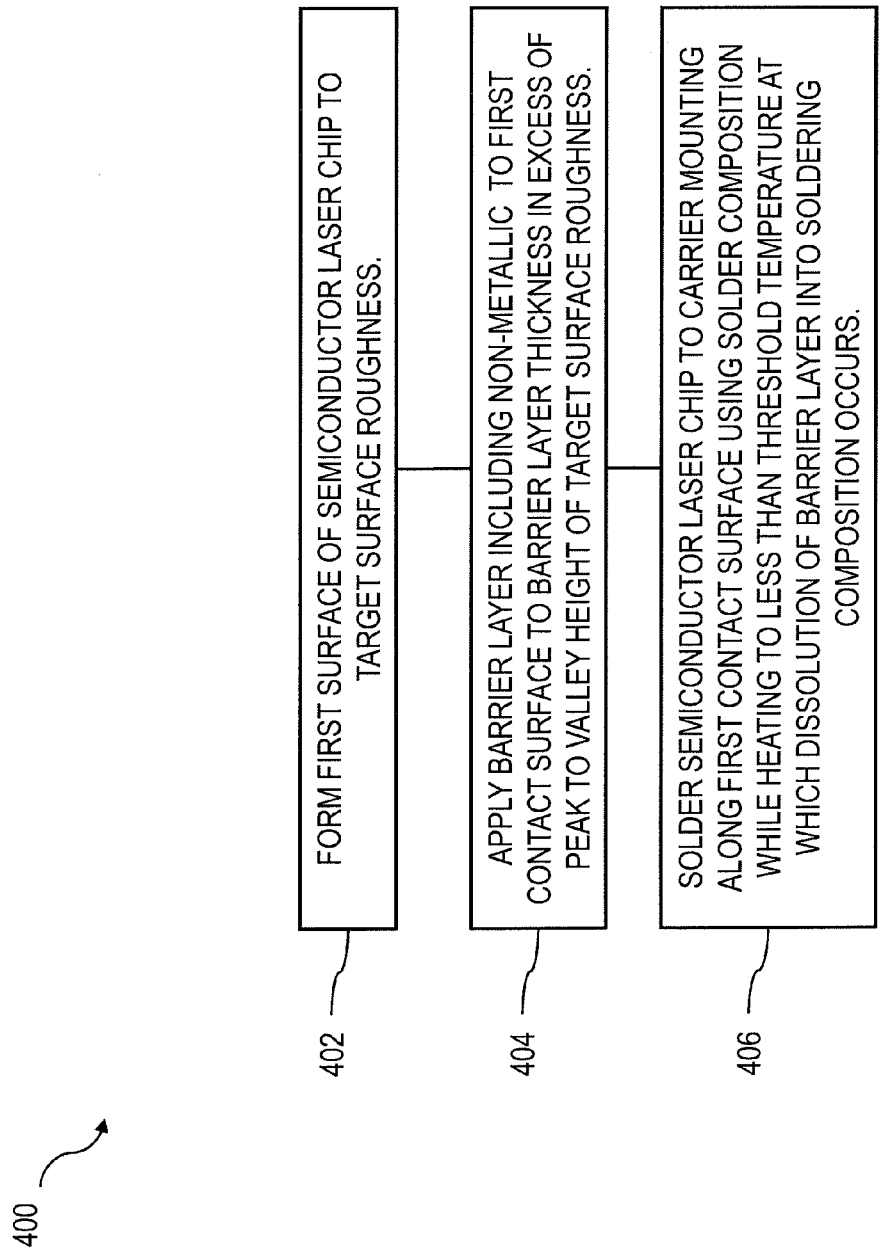
FIG. 4 is a process flow diagram illustrating aspects of a method having one or more features consistent with implementations of the current subject matter.

FIG. 4 shows a process flow chart illustrating a method including features that can be present in one or more implementations of the current subject matter. At 402, a first contact surface of a semiconductor laser chip is formed to a target surface roughness. The target surface roughness is selected to have a maximum peak to valley height that is substantially smaller than a barrier layer thickness of a barrier layer to be applied to the first contact surface. At 404, that barrier layer is applied to the first contact surface with the barrier layer thickness. The barrier layer includes the at least one non-metallic, electrically-conducting compound, examples of which include but are not limited to titanium nitride ($TiN_x$), titanium oxy-nitride ($TiN_xO_y$), cerium gadolinium oxy-nitride ($CeGdO_yN_x$) cerium oxide ($CeO_2$), and tungsten nitride ($WN_x$). At 406, the semiconductor laser chip is soldered to a carrier mounting along the first contact surface using a solder composition. The soldering includes melting the soldering composition by heating the soldering composition to less than a threshold temperature at which dissolution of the barrier layer into the soldering composition occurs.

In some implementations, a contact surface 310 of a laser semiconductor chip 302 can be polished or otherwise prepared to have a target surface roughness of less than approximately 100 Å rms, or alternatively of less than approximately 40 Å rms. Conventional approaches have typically not focused on the surface roughness of the contact surface 310 and have consequently had surface roughness values of greater than approximately 1 μm rms. Subsequent to preparing a sufficiently smooth contact surface 310, the contact surface 310 can be treated to form one or more barrier layers.

Creation of a barrier layer that can survive the soldering process can be aided by polishing of the first contact surface 310 to a low surface roughness. In general, a total thickness of a metallic barrier layer, for example one made of platinum, may only be deposited at a limited thickness due to very high stresses that can lead to a separation of thicker layers from the semiconductor material of the semiconductor laser chip 302. The barrier layer can include multiple layers of differing materials. In an implementation, at least one of the barrier layers can include a non-metallic, electrically conducting compound, such as for example titanium nitride ($TiN_x$), titanium oxy-nitride ($TiN_xO_y$), cerium gadolinium oxy-nitride ($CeGd_yON_x$), cerium oxide ($CeO_2$), and tungsten nitride ($WN_x$). One or more additional barrier layers overlaying or underlaying the first barrier layer can include a metal including but not limited to platinum (Pt), palladium (Pd), nickel (Ni), tungsten (W), molybdenum (Mo) titanium (Ti), tantalum (Ta), zirconium (Zr), cerium (Ce), gadolinium (Gd), chromium (Cr), manganese (Mn), aluminum (Al), beryllium (Be), and Yttrium (Y).

A solder composition can in some implementations be selected from a composition having a liquidus temperature, i.e. the maximum temperature at which solid crystals of an alloy can co-exist with the melt in thermodynamic equilibrium, of less than approximately 400° C., or optionally of less than approximately 370° C., or optionally of less than approximately 340° C. Examples of solder compositions consistent with one or more implementations of the current subject matter can include, but are not limited to gold germanium (AuGe), gold silicon (AuSi), gold tin (AuSn), silver tin (AgSn), silver tin copper (AgSnCu), silver tin lead (AgSnPb), silver tin lead indium (AgSnPbIn), silver tin antimony (AgSnSb), tin lead (SnPb), and lead (Pb). Examples of specific solder compositions that are consistent with one or more implementations of the current subject matter include, but are not limited to the following: approximately 48% Sn and approximately 52% In; approximately 3% Ag and approximately 97% In; approximately 58% Sn and approximately 42% In; approximately 5% Ag, approximately 15% Pb, and approximately 80% In; approximately 100% In; approximately 30% Pb and approximately 70% In; approximately 2% Ag, approximately 36% Pb, and approximately 62% Sn; approximately 37.5% Pb, approximately 37.5% Sn, and approximately 25% In; approximately 37% Pb and approximately 63% Sn; approximately 40% Pb and approximately 60% In; approximately 30% Pb and approximately 70% Sn; approximately 2.8% Ag, approximately 77.2% Sn, and approximately 20% In; approximately 40% Pb and approximately 60% Sn; approximately 20% Pb and approximately 80% Sn; approximately 45% Pb and approximately 55% Sn; approximately 15% Pb and approximately 85% Sn; approximately 50% Pb and approximately 50% In; approximately 10% Pb and approximately 90% Sn; approximately 10% Au and approximately 90% Sn; approximately 3.5% Ag and approximately 96.5% Sn; approximately 60% Pb and approximately 40% In; approximately 3.5% Ag, approximately 95% Sn, and approximately 1.5% Sb; approximately 2.5% Ag and approximately 97.5% Sn; approximately 100% Sn; approximately 99% Sn and approximately 1% Sb; approximately 60% Pb and approximately 40% Sn; approximately 97% Sn and approximately 3% Sb; approximately 95% Sn and approximately 5% Sb; approximately 63.2% Pb, approximately 35% Sn, and approximately 1.8% In; approximately 70% Pb and approximately 30% Sn; approximately 75% Pb and approximately 25% In; approximately 80% Pb approximately 20% Sn; approximately 81% Pb and approximately 19% In; approximately 80% Au and approximately 20% Sn; approximately 86% Pb, approximately 8% Bi, approximately 4% Sn, and approximately 1% In, approximately 1% Ag; approximately 85% Pb and approximately 15% Sn; approximately 2% Ag, approximately 88% Pb, and approximately 10% Sn; approximately 5% Ag, approximately 90% Pb, and approximately 5% Sn; approximately 95% Pb and approximately 5% Sb; approximately 2.5% Ag, approximately 92.5% Pb, and approximately 5% Sn; approximately 2.5% Ag, approximately 92.5% Pb, and approximately 5% In; approximately 90% Pb and approximately 10% Sn; approximately 2.5% Ag and approximately 97.5% Pb; approximately 2.5% Ag; approximately 95.5% Pb, and approximately 2% Sn; approximately 78% Au and approximately 22% Sn; approximately 1.5% Ag, approximately 97.5% Pb, and approximately 1% Sn; approximately 5% Ag, approximately 90% Pb, and approximately 5% In; approximately 95% Pb and approximately 5% In; and approximately 95% Pb and approximately 5% Sn.

Figure 5:
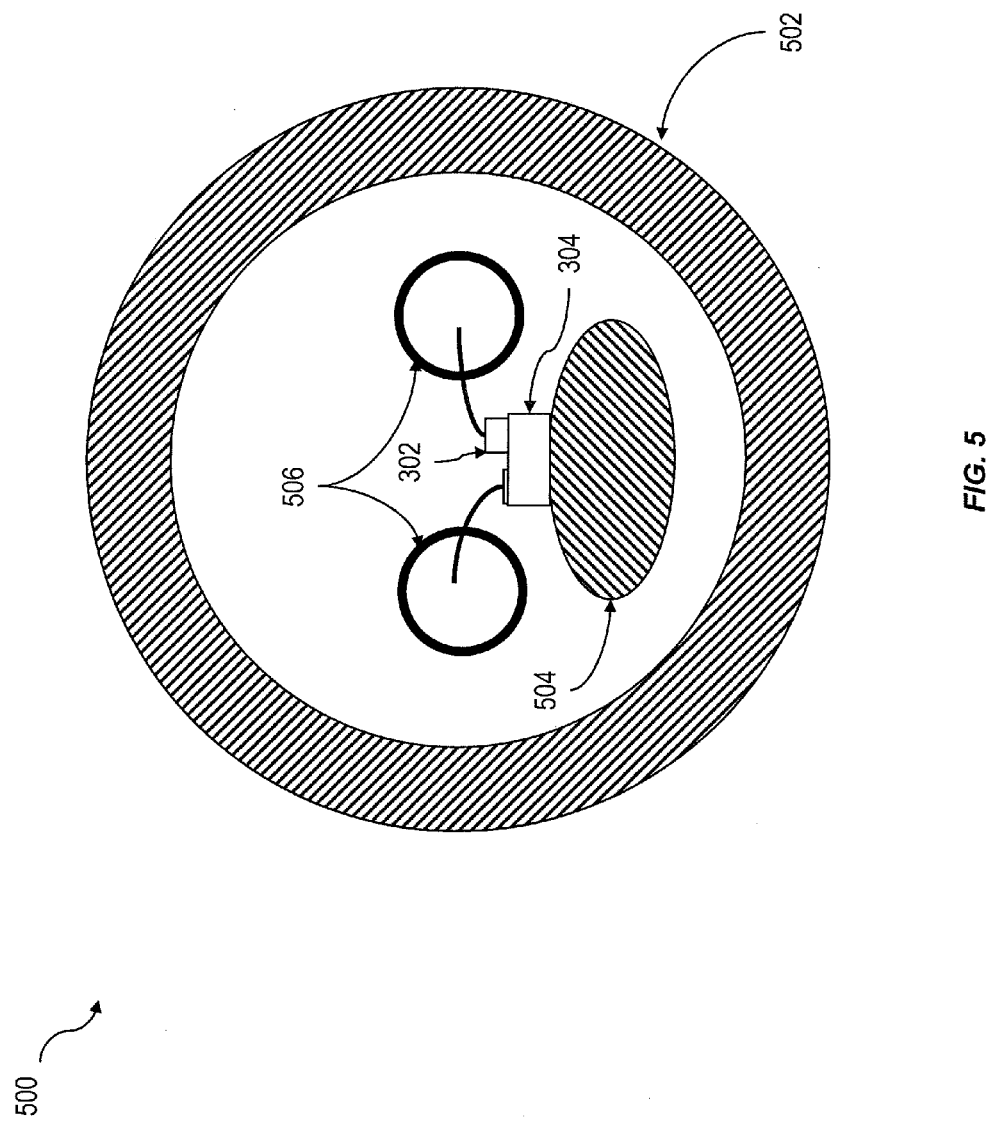
FIG. 5 is a diagram showing an end elevation view of a conventional TO-can mount such as are typically used for mounting semiconductor laser chips.
Figure 6:
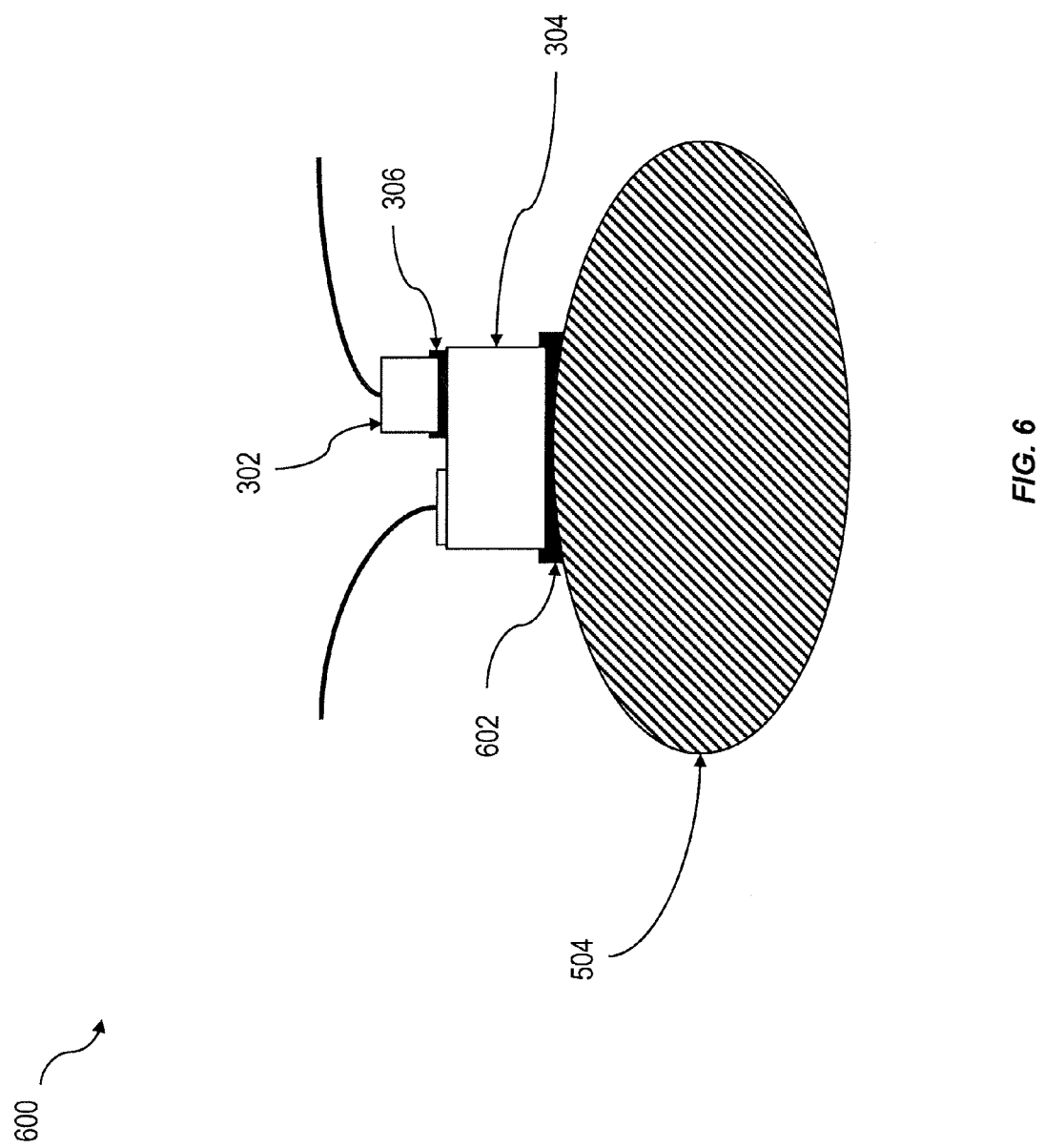
FIG. 6 is a diagram showing a magnified view of a carrier mount and a semiconductor laser chip affixed thereto.

FIG. 5 shows an end elevation view of a conventional transistor outline can (TO-can) mount 500 such as is typically used in mounting of semiconductor laser chips for use in telecommunications applications. TO-cans are widely used electronics and optics packaging platforms used for mechanically mounting, electrically connecting, and heat sinking semiconductor chips such as lasers and transistors and are available in a variety of different sizes and configurations. An outer body 502 encloses a post or heat sink member 504 which can be made of metal, such as for example a copper tungsten sintered metal, copper-diamond sintered metal, or iron-nickel alloys including Kovar, alloy 42, and alloy 52. Two insulated electrical pass-throughs 506 can be included to provide electrical contacts for connection to the p and n junctions on a semiconductor laser chip 302. The semiconductor laser chip 302 can be mounted to a carrier sub-mount, which can in some examples be formed of silicon. As noted above, the semiconductor laser chip 302 can be joined to the carrier mount 304 (also referred to as a carrier mounting) by a layer of solder 306, which is not shown in FIG. 5 due to scale constraints. FIG. 6 shows a magnified view 600 of the post or heat sink member 504, the carrier mount 304, the semiconductor laser chip 302, and the solder 306 joining the semiconductor laser chip 302 to the carrier mount. The carrier mount 304 can in turn be soldered to the post or heat sink member 504 by a second solder layer 602.

According to one or more implementations of the current subject matter, mono-component layers (or surfaces) of a material dissimilar from the solder preparation layer, which includes but is not limited to gold, can serve similarly as solder alloys, enabling low temperature joining of two gold surfaces for instance. In joining metal components, this is commonly referred to as liquidus or liquid diffusion bonding since it apparently creates a very thin liquid interface layer between certain dissimilar metals which are brought in physical contact under elevated temperature. The temperature necessary to cause this effect to occur is typically significantly lower than the component melting temperatures. Once the initial joining has taken place, thermal separation can typically require quite high temperatures, approaching or reaching the component melting temperatures. In one example, contact between a silver surface and a gold surface can result in a hermetic joint at a temperature of approximately 150° C. to approximately 400° C., which is significantly lower than the separate melting temperatures of silver (950° C.) and gold (1064° C.). In another example, copper oxide can serve as a bonding promotion layer which can reduce a joining temperature between two metal surfaces significantly below the metal melting points.

Thus, in some implementations, solder compositions including lead (Pb), silver (Ag), silicon (Si), germanium (Ge), tin (Sn), antimony (Sb), bismuth (Bi), indium (In), and copper (Cu) as well as those discussed elsewhere herein can be used in association with deposition of one or more solder-facilitating mono-component material layers or thin sheets (e.g. preforms) on the first contact surface 310 and/or second contact surface 314 prior to the soldering process. The one or more solder-facilitating mono-component material layers or thin sheets can be dissimilar from other barrier and/or metallization layers on the first contact surface 310 and/or second contact surface 314. One example of a method for applying solder-facilitating mono-component material layers or thin sheets can include depositing a thin layer of a metal differing from those metals present in the solder preparation layer on top of the barrier and/or metallization layers on the first contact surface 310 and/or second contact surface 314. Such a thin layer can be evaporated or otherwise deposited onto one or both of the first contact surface 310 and the second contact surface 314 shortly before the heat assisted joining process takes place, in order to prevent or minimize oxidation. Alternately, a thin sheet of a metal dissimilar from the solder preparation layer can be placed between the semiconductor laser chip 302 and the mounting device 304. The soldering process can then proceed as discussed above.

Figure 7:
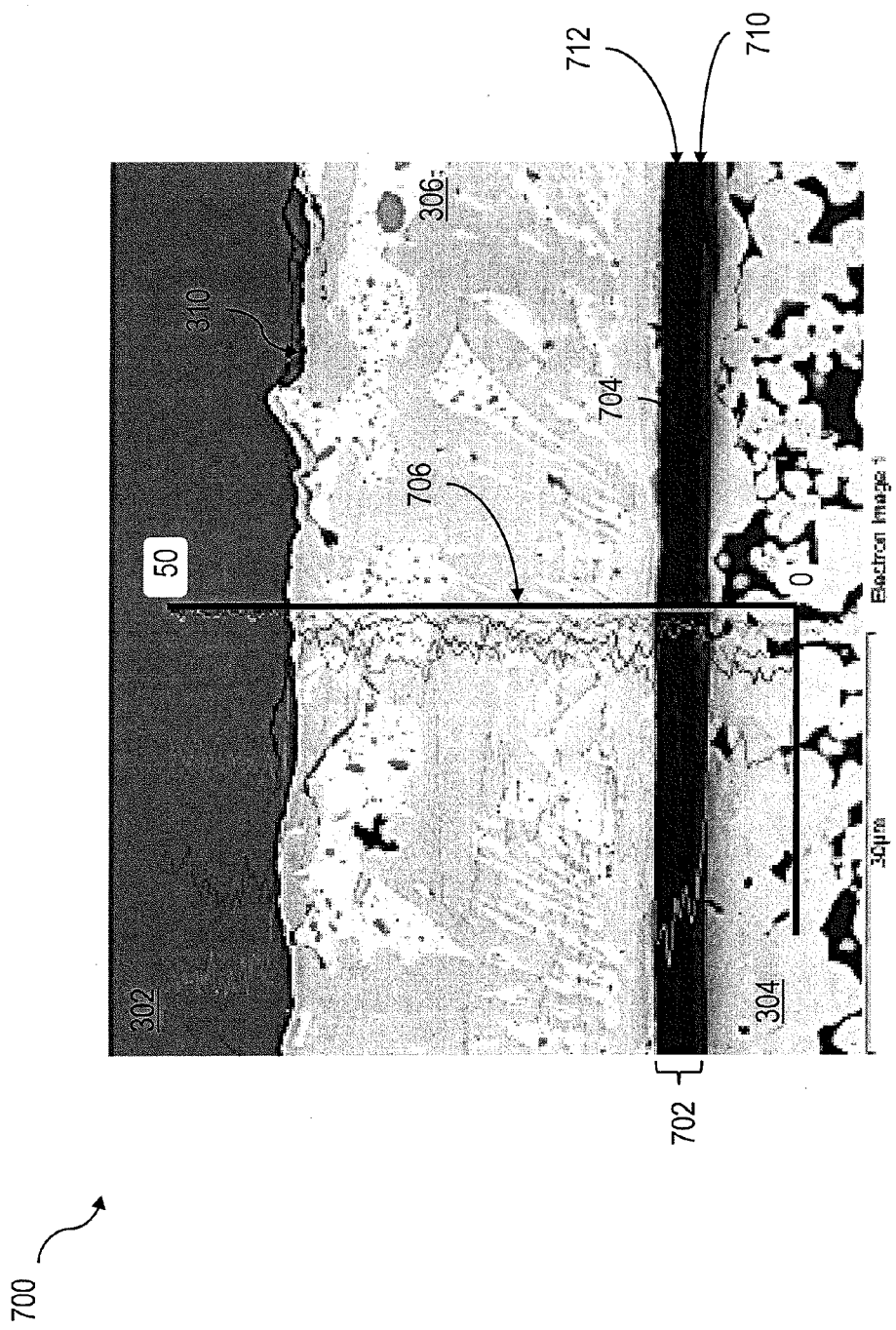
FIG. 7 is a scanning electron micrograph showing a solder joint between a semiconductor laser chip and a carrier mount.

FIG. 7 shows an electron micrograph 700 showing a highly magnified solder layer 306 interposed between a semiconductor laser chip 302 and a carrier mount 304. A second barrier layer 702 of nickel is also provided on the second contact surface 704 of the carrier mount 304. A vertical axis 706 is displayed atop the electron micrograph to delineate distance from an arbitrarily chosen origin coordinate (marked as "0" on the axis 706) to a linear distance of 50 microns away (marked as "50" on the axis 706). The semiconductor laser chip 302 shown in FIG. 7 was not prepared with a smooth first contact surface 310 as described herein consistent according various implementations of the current subject matter. As a result, the first contact surface 310 exhibits substantial surface roughness, and no contiguous barrier layer remains to separate the material of the semiconductor laser chip 302 from the solder after the soldering process. FIG. 8 through FIG. 14 show a series of charts 800, 900, 1000, 1100, 1200, 1300, and 1400 showing relative concentrations of phosphorous, nickel, indium, tin, lead, tungsten, and gold, respectively, as a function of distance along the axis 706 in FIG. 7. The relative concentrations were determined by an X-ray diffraction technique.

Figure 8:
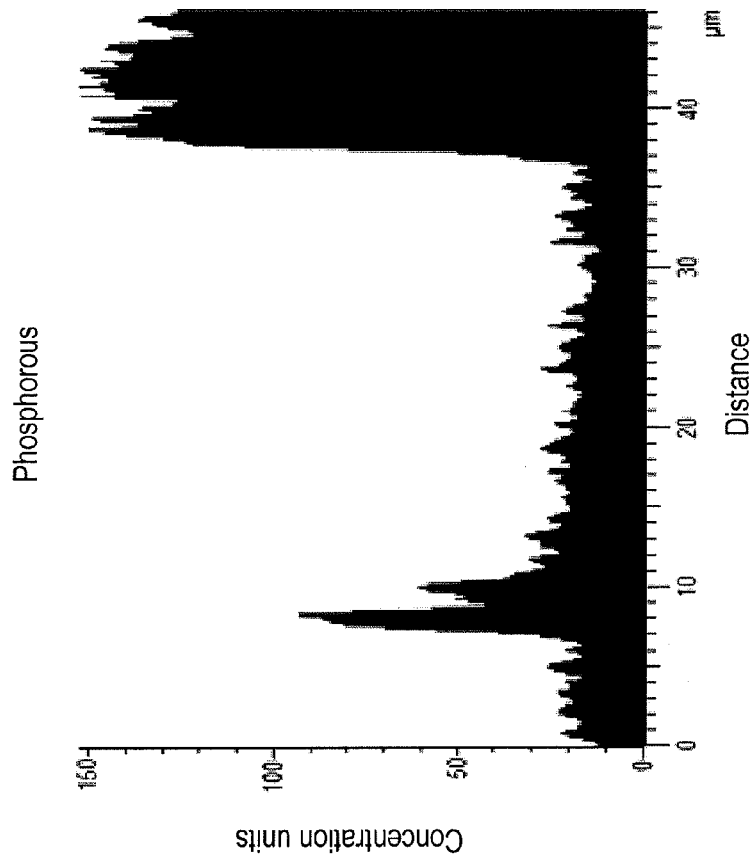
FIG. 8 is a chart showing a phosphorous concentration measured by X-ray diffraction as a function of depth in the apparatus shown in FIG. 7.

As shown in the chart 800 of FIG. 8, a large phosphorous concentration is observed in the semiconductor laser chip 302 (distance greater than about 36 μm) due to the semiconductor laser chip 302 being a crystal of indium phosphide (InP). Additional high relative concentrations of phosphorous are observed in the nickel barrier layer 702, which is actually formed of a first layer 710 of nickel deposited by an electroless process that incorporates some phosphorous into the deposited nickel and a second layer of nickel deposited by an electrolytic process that incorporates less or no phosphorous into the deposited nickel. A non-zero concentration of phosphorous occurs both in the solder (which is composed of a tin-lead alloy and does not contain any phosphorus in its original state) and in the electrolytic second layer 712 of nickel. These non-zero concentrations are respectively due to diffusion of phosphorous from the crystal structure of the semiconductor laser chip 302 and from the electroless first layer 710 of nickel.

Figure 9:
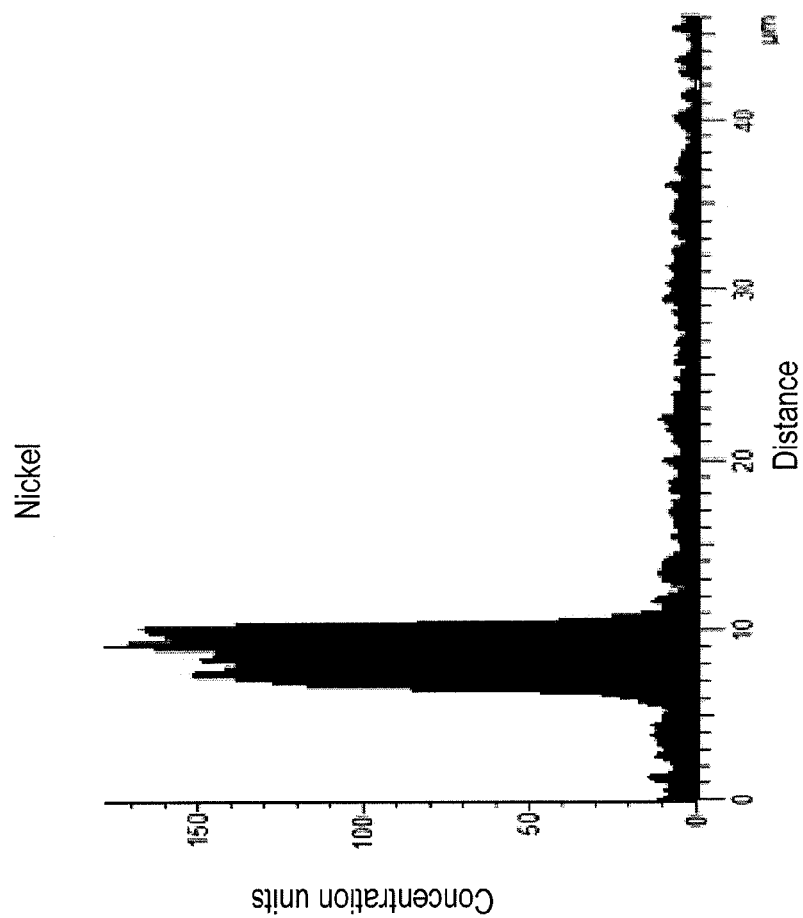
FIG. 9 is a chart showing a nickel concentration measured by X-ray diffraction as a function of depth in the apparatus shown in FIG. 7.
Figure 10:
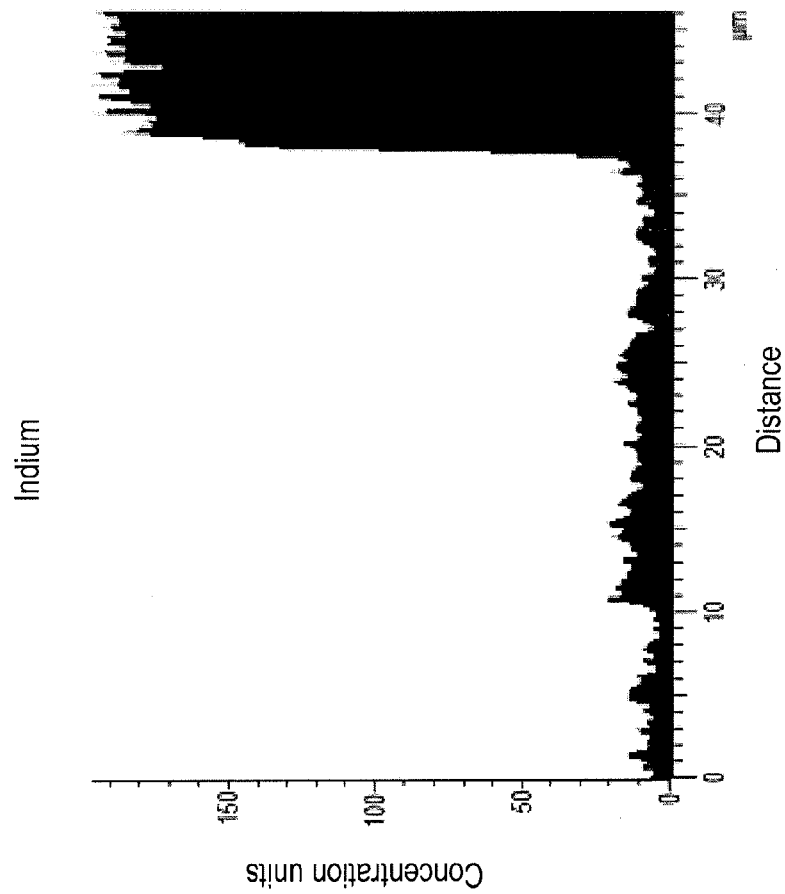
FIG. 10 is a chart showing an indium concentration measured by X-ray diffraction as a function of depth in the apparatus shown in FIG. 7.
Figure 11:
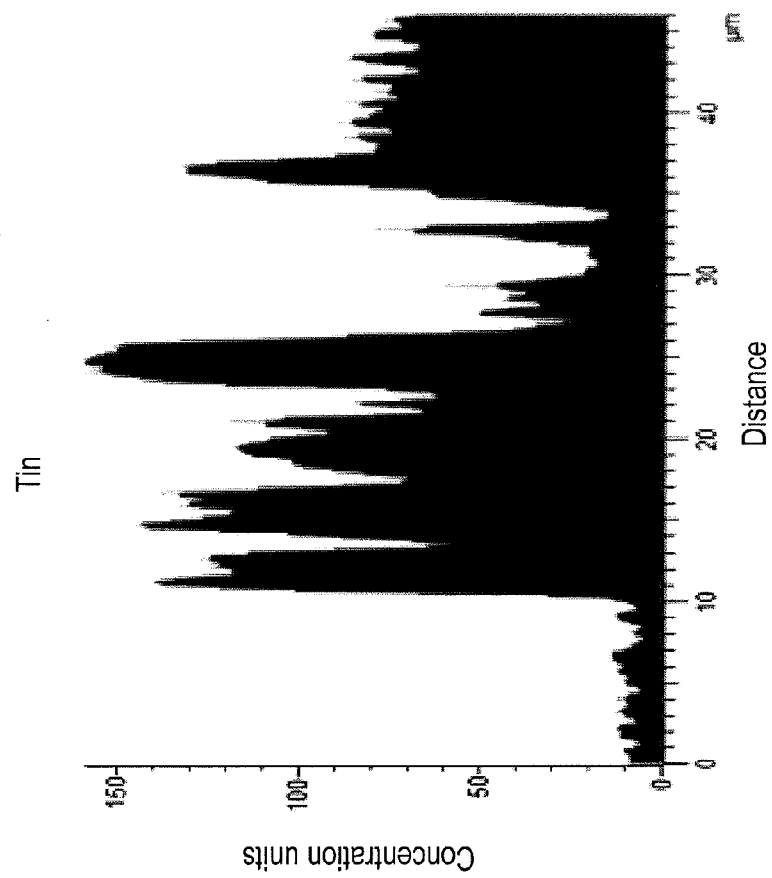
FIG. 11 is a chart showing a tin concentration measured by X-ray diffraction as a function of depth in the apparatus shown in FIG. 7.
Figure 12:
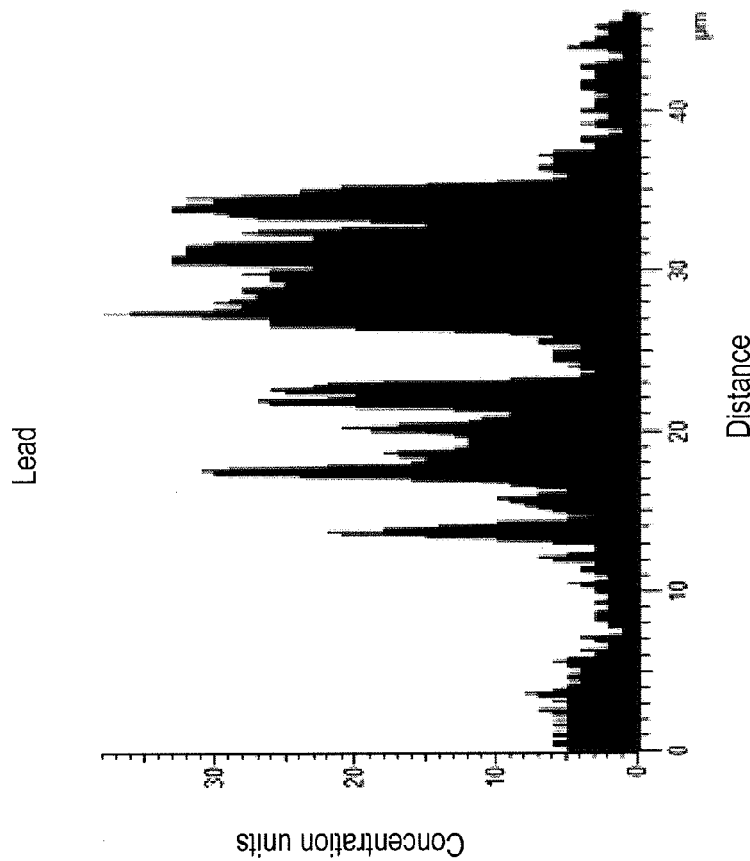
FIG. 12 is a chart showing a lead concentration measured by X-ray diffraction as a function of depth in the apparatus shown in FIG. 7.
Figure 13:
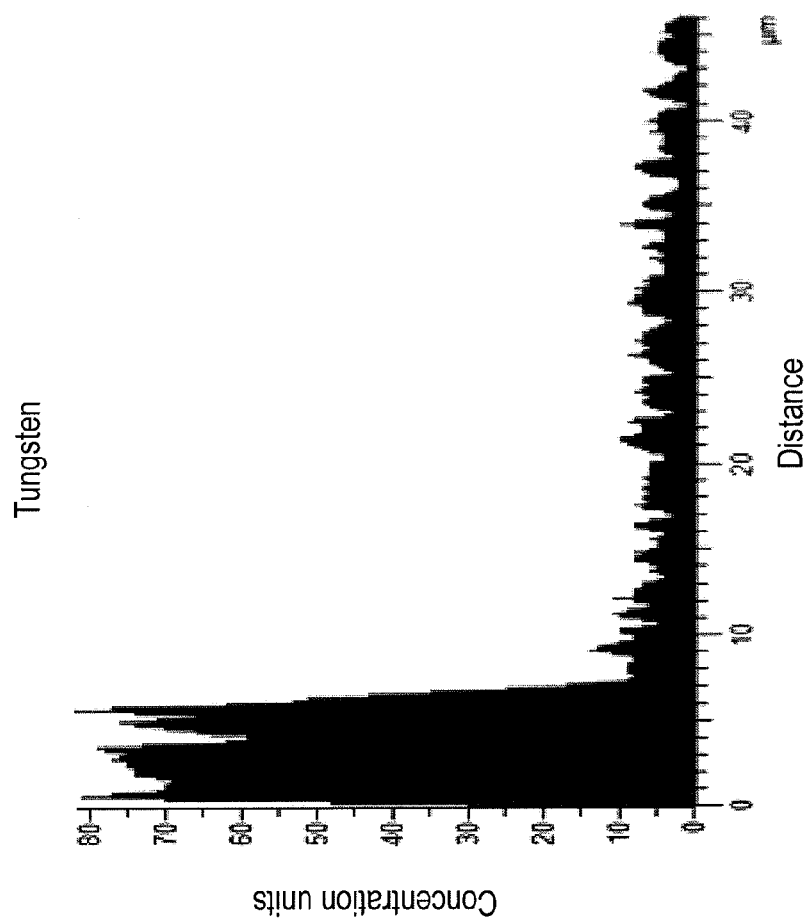
FIG. 13 is a chart showing a tungsten concentration measured by X-ray diffraction as a function of depth in the apparatus shown in FIG. 7.
Figure 14:
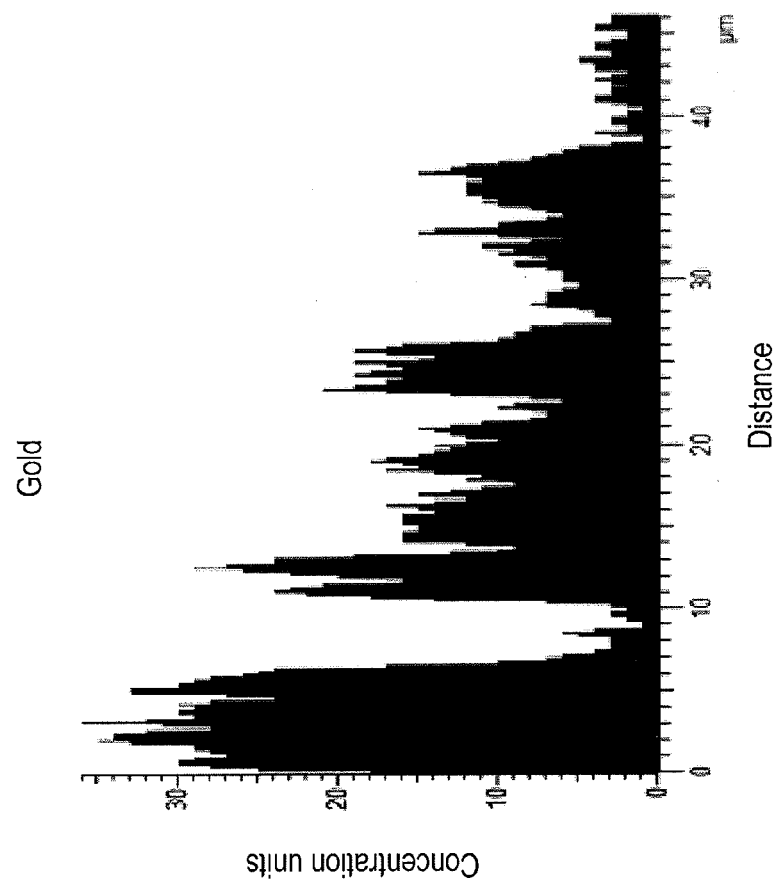
FIG. 14 is a chart showing a gold concentration measured by X-ray diffraction as a function of depth in the apparatus shown in FIG. 7; and When practical, similar reference numbers denote similar structures, features, or elements.

FIG. 9 illustrates that some nickel also diffuses into the solder 306 from the nickel layer 702 and further into the crystal structure of the semiconductor laser chip 302. Similarly, indium diffuses into the solder 306 and from there into the carrier mount across the nickel barrier layer 702 as shown in the chart 1000 of FIG. 10. Tin, which is a primary component of the solder 306, does not remain in the solder 306, but also diffuses into the crystal structure of the semiconductor laser chip 302 as shown in the chat 1100 of FIG. 11. Lead also diffuses out of the solder layer 306 as shown in the chart 1200 of FIG. 12, but to a lesser degree than does the tin from the solder 306. Tungsten from the tungsten-copper carrier mount 304 and gold from solder preparation layers deposited on both of the first contact surface 310 and the second contact surface 702 diffuse into the solder and to a small extent into the semiconductor laser chip 302 as shown in the charts 1300 and 1400 of FIG. 13 and FIG. 14.

Accordingly, features of the current subject matter that allow the maintenance of a contiguous, intact barrier layer at least at the first contact surface 310 of the semiconductor laser chip 302, and also desirably at the second contact surface 704 of the carrier mount 304 can be advantageous in minimizing diffusion of elements from the carrier mount and/or semiconductor laser chip across the barrier layer and can thereby aid in maintaining a more temporally consistent composition of both the solder layer 306 and the crystal structure of the semiconductor laser chip 302. The presence of phosphorous and/or other reactive compounds or elements, such as for example oxygen, antimony, silicon, iron and the like in the solder layer 306 can increase a tendency of the solder alloy components to react and thereby change in chemical composition, in crystal structure, hermeticity and, more importantly, in electrical and/or thermal conductivity. Such changes can lead to alteration in the laser emission characteristics of a semiconductor laser chip 302 in contact with the solder layer 306.

Furthermore, diffusion of solder components, such as for example lead; silver; tin; and the like; and/or carrier mount components such as tungsten, nickel, iron, copper and the like, into the crystal structure of the semiconductor laser chip 302 can also cause changes in the laser emission characteristics over time.

Implementations of the current subject matter can provide one or more advantages, including but not limited to maintaining a contiguous diffusion barrier layer between a laser crystal or other semiconductor chip and its physical mounting, preventing inter-diffusion of solder compounds into the laser crystal and vice versa, and preventing contamination of the solder. Inter-diffusion and/or electro-migration have been found to cause changes in the electrical resistivity, and to a lesser extent the heat conduction properties, of the contact. Very small changes in resistive heating of even one of the electrical contacts providing a driving current to a semiconductor laser chip can lead to frequency changes in the light produced by the semiconductor laser chip.

In some observed examples using conventional semiconductor laser chip mounting approaches, induced shifts in the laser output can be greater than a picometer per day. Implementations of the current subject matter can therefore include one or more techniques for improving barrier layers at one or more of the first contact surface 310 between the solder layer 306 and the semiconductor laser chip 302 and the second contact layer 702 between the solder layer 306 and the carrier mount 304. In one example, an improved barrier layer at the second contact surface 702 can include an electroless plated nickel underlayer 710, for example to preserve edge definition of a copper tungsten submount or the like, covered by a minimum thickness of an electrolytic nickel layer 712 as the final layer before deposition of a gold solder preparation layer. In another example, a single layer of a sputtered barrier material, including but not limited to at least one of nickel, platinum, palladium, and electrically conducting non-metallic barrier layers, can be used as a single barrier layer at the first contact surface 310. As oxidation of the solder material prior to soldering of the semiconductor laser chip 302 to the carrier mount 304 can introduce oxygen and other potentially reactive contaminants, it can be advantageous to use solder forms that have not been allowed to substantially oxidize prior to use. Alternatively, the soldering process can be performed under a non-oxidizing atmosphere or under a reducing atmosphere including but not limited to vacuum, pure nitrogen pure hydrogen gas ($H_2$), forming gas (approximately 5% hydrogen in 95% nitrogen), and formic acid in nitrogen carrier gas to remove or at least reduce the presence of oxidized compounds in the solder composition on the metalized semiconductor contact surface and the carrier mounting surface.

Suitable barrier layers to be deposited on the first contact surface 310 and/or the second contact surface 702 can include, but are not limited to, platinum (Pt), palladium (Pd), nickel (Ni), titanium nitride ($TiN_x$), titanium oxy-nitride ($TiN_xO_y$), tungsten nitride ($WN_x$), cerium oxide ($CeO_2$), and cerium gadolinium oxy-nitride ($CeGdO_yN_x$). These compounds, as well as other comparable compounds that can be deposited by sputtering or vapor deposition onto the first and/or second contact surfaces, can provide a barrier layer that has a sufficiently high temperature resistance during the soldering process as to not dissolve in the solder or otherwise degrade sufficiently to cause breakdown of the barrier qualities necessary to prevent cross-barrier diffusion of semiconductor laser materials into the solder or solder components into the semiconductor laser crystal. The second barrier layer 702 applied to the second contact surface 704 can in some implementations include a sintered diamond-copper layer. A process for creation of a non-metallic, electrically-conducting barrier layer 702 can include first depositing titanium via a thin film deposition process, including but not limited to sputtering, electron beam evaporation, chemical vapor deposition, atomic layer deposition, and the like, and then adding nitrogen to react with the deposited titanium. In another implementation, a first metallization layer can be deposited by a thin film deposition process, and nitrogen ions can be used for sputtering titanium, for example in a nitrogen gas background, to create the non-metallic barrier layer. Chemical vapor deposition can also or alternatively be used to create non-metallic barrier layers. In another implementation, gas phase reactions of the components elements or compounds forming the non-metallic electrically conductive compound can be used to create multi-component non-metallic barrier layers.

In some implementations, the heat conductivity of a carrier mount 304 can advantageously exceed 50 Watts per meter-Kelvin or, optionally 100 Watts per meter-Kelvin or, optionally 150 Watts per meter-Kelvin. Suitable carrier mount materials can include, but are not limited to copper tungsten, tungsten, copper-diamond, aluminum nitride, silicon, silicon nitride, silicon carbide, beryllium oxide, alumina ($Al_2O_3$), Kovar, Alloy 42, Alloy 52, and the like. A heat spreader or carrier mount 304 that is thermally expansion matched to the semiconductor laser chip 302 can be used in some implementations. In one example consistent with an implementation of the current subject matter, an approximately 15% copper, approximately 85% tungsten sintered metal heat spreader, a beryllium oxide heat spreader, an alumina heat spreader, a sapphire heat spreader, a copper-diamond heat spreader, or the like can provide a good thermal expansion match to a gallium antimonide (GaSb) semiconductor laser chip 302 at around approximately 7 ppm $°C.^{-1}$. In another example consistent with an implementation of the current subject matter, a pure tungsten heat spreader, a silicon heat spreader, a silicon nitride heat spreader, a silicon carbide heat spreader, a sapphire heat spreader, a copper diamond heat spreader, or an aluminum nitride (AlN) heat spreader can be used as a carrier mount 304 to provide a good thermal expansion match to an indium phosphide (InP) semiconductor laser chip 302 at around 4.5 ppm $°C.^{-1}$. A silicon, silicon carbide, silicon nitride, aluminum nitride, tungsten, copper diamond heat spreader, or the like can also be used as the carrier sub-mount 304, for example for an indium phosphide (InP) semiconductor laser chip 302.

Other carrier mounts consistent with implementations of the current subject matter include, but are not limited to shaped copper tungsten heat spreaders, including but not limited to semiconductor laser industry standard c-mounts and CT-mounts, TO-cans, pattern metallized ceramics, pattern metallized silicon, pattern metallized silicon carbide, pattern metallized silicon nitride, pattern metallized beryllium oxide, pattern metallized alumina, pattern metallized aluminum nitride, copper-diamond, pure copper with one or more sections of expansion-matched submounts to match to one or more semiconductor laser chip compositions, tungsten submounts brazed into a copper or copper tungsten c-mount, or the like. Semiconductor laser chips 302 can be formed, without limitation of indium phosphide crystals, gallium arsenide crystals, gallium antimonide crystals, gallium nitride crystals, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An article of manufacture comprising:
    a first contact surface of a semiconductor laser chip formed to a target surface roughness having a maximum peak to valley height of between approximately 2% and 8% of a barrier layer thickness;
    a barrier layer having the barrier layer thickness applied to the first contact surface, the barrier layer being distinct from the semiconductor laser chip and comprising a non-metallic, electrically-conducting compound; and
    a carrier mounting to which the semiconductor laser chip is soldered along the barrier layer using a solder composition, the semiconductor laser chip being soldered to the carrier mounting by a soldering process comprising melting the soldering composition by heating the soldering composition to less than a threshold temperature at which dissolution of the barrier layer into the soldering composition occurs, the soldering process occurring such that the barrier layer remains intact to minimize diffusion of elements from the carrier mount, the solder composition, and/or the semiconductor laser chip across the barrier layer to maintain a substantially temporally consistent composition of both the solder composition along the first contact surface and a crystal structure of the semiconductor laser chip.

2. The article of manufacture of claim 1, wherein, subsequent to the soldering process, the barrier layer remains substantially contiguous such that no direct path exists by which constituents of the semiconductor laser chip can diffuse into the solder composition.

3. The article of manufacture of claim 1, wherein, subsequent to the soldering process, the barrier layer remains substantially contiguous such that no direct path exists by which constituents of any of the semiconductor laser chip, the solder composition, and the carrier mounting can diffuse across the barrier layer.

4. The article of manufacture of claim 1, wherein, subsequent to the soldering process, the solder composition is characterized by substantially temporally stable electrical and thermal conductivities.

5. The article of manufacture of claim 1, wherein, prior to the soldering process, the solder composition comprises at least one of a solder preform that is substantially non-oxidized and a deposited layer that is substantially non-oxidized.

6. The article of manufacture of claim 1, wherein the soldering process further comprises performing the melting of the soldering composition under at least one of a reducing atmosphere and a non-oxidizing atmosphere.

7. The article of manufacture of claim 1, wherein the solder composition is selected from a group consisting of gold germanium (AuGe), gold silicon (AuSi), gold tin (AuSn), silver tin (AgSn), silver tin copper (AgSnCu), silver tin lead (AgSnPb), silver tin lead indium (AgSnPbIn), silver tin antimony (AgSnSb), tin lead (SnPb), lead (Pb), silver (Ag), silicon (Si), germanium (Ge), tin (Sn), antimony (Sb), bismuth (Bi), indium (In), and copper (Cu).

8. The article of manufacture of claim 1, wherein the non-metallic, electrically-conducting compound comprises at least one of titanium nitride ($TiN_X$), titanium oxy-nitride ($TiN_XO_Y$), tungsten nitride ($WN_X$), cerium oxide ($CeO_2$) and cerium gadolinium oxy-nitride ($CeGdON_X$).

9. The article of manufacture of claim 1, wherein the forming of the first contact surface to the target surface roughness comprises polishing the first contact surface to achieve the target surface roughness prior to applying the barrier layer.

10. The article of manufacture of claim 1, wherein the target surface roughness is less than approximately 40 Å rms.

11. The article of manufacture of claim 1, wherein a first thermal expansion characteristic of the carrier mounting is matched to a second thermal expansion characteristic of the semiconductor laser chip.

12. The article of manufacture of claim 1, further comprising:
   a metallization layer applied to the first contact surface prior to applying the barrier layer; and
   a solder preparation layer applied to the first contact surface subsequent to applying the non-metallic, electrically-conducting barrier layer and prior to the soldering process.

13. The article of manufacture of claim 12, wherein the metallization layer comprises approximately 600 Å thickness of titanium, the non-metallic, electrically-conducting barrier layer comprises approximately 1200 Å thickness of one or more of titanium nitride ($TiN_X$), titanium oxy-nitride ($TiN_XO_Y$), tungsten nitride (WNx), cerium oxide ($CeO_2$) and cerium gadolinium oxy-nitride ($CeGdON_X$); and the solder preparation layer comprises approximately 2000 to 5000 Å thickness of gold.

14. The article of manufacture of claim 1, further comprising a second metallic barrier layer applied to the first contact surface, the second, metallic barrier layer comprising at least one of platinum (Pt), palladium (Pd), nickel (Ni), tungsten (W), molybdenum (Mo), titanium (Ti), tantalum (Ta), zirconium (Zr), cerium (Ce), gadolinium (Gd), chromium (Cr), manganese (Mn), aluminum (Al), beryllium (Be), and Yttrium (Y).

15. The article of manufacture of claim 1, further comprising a second barrier layer applied to a second contact surface of the carrier mounting, the soldering of the semiconductor laser chip being performed along the second contact surface.

16. The article of manufacture of claim 1, further comprising a solder facilitation layer added between the first contact surface and a second contact surface on the carrier mounting prior to the soldering, the solder facilitation layer comprising a metal that is not a component of a solder preparation layer on either or both of the first contact surface and a second contact surface.

17. The article of manufacture of claim 16, wherein the solder facilitation layer is added by at least one of placing a sheet of the metal between the first contact surface and the second contact surface prior to the soldering, and depositing a layer of the metal that is not a component of the solder composition onto one or both of the first contact surface and the second contact surface prior to the soldering.

18. The article of manufacture of claim 1, further comprising:
   a light source that comprises the carrier mounting and the semiconductor laser chip;
   a detector that quantifies a received intensity of light emitted from the light source along a path length;
   at least one of a sample cell and a free space volume through which the path length passes at least once; and
   at least one processor that performs operations comprising controlling a driving current to the laser source and receiving intensity data from the detector.

\* \* \* \* \*